United States Patent [19]

Schwartz et al.

[11] Patent Number: 4,971,915

[45] Date of Patent: Nov. 20, 1990

[54] SIMULATED DISTILLATION OF PETROLEUM RESIDUES BY CAPILLARY SFC

[75] Inventors: Herbert E. Schwartz, San Carlos; Robert G. Brownlee, Los Altos, both of Calif.

[73] Assignee: Applied Biosystems, Inc., Foster City, Calif.

[21] Appl. No.: 50,755

[22] Filed: May 15, 1987

[51] Int. Cl.⁵ ............................................. G01N 33/00
[52] U.S. Cl. ..................................... 436/139; 436/161
[58] Field of Search ............................. 436/60, 25–33, 436/139–144, 161, 807

[56] References Cited

U.S. PATENT DOCUMENTS 4,159,894  7/1979  Hu ......................................... 436/60
4,388,407  6/1983  Lepain et al. ......................... 436/60
4,388,408  6/1983  Sien et al. .............................. 436/60

FOREIGN PATENT DOCUMENTS 0142558  9/1982  Japan ..................................... 436/60

OTHER PUBLICATIONS

Integral Pressure Restrictor for Capillary SFC by E. J. Guthrie and H. E. Schwartz, Jun. 1986.
Ferguson and O'Brien, *Journal of Chromatography*, 1981, "Characterisation of 'Deasphaltened' Petroleum Residues by Gel Permeation Chromatography".
Lauer, McManigill, & Board, *Analytical Chemistry*, Jul. 1983, "Mobile-Phase Transport Properties of Liquefied Gases in Near-Critical and Supercritical Fluid Chromatography".
Southern, Lacchelli, Cuthiell, Selucky, *Analytical Chemistry*, 1985 "Simulated Distillation of Coal-Derived Liquid Using Combined Gas Chromatography-Vacuum Thermogravimetry".
Chester, Innis, *Journal of High Resolution Chromatography and Chromatography Communications*, 1985, "Retention in Capillary Supercritical Fluid Chromatography".
Schwartz and Brownlee, *Journal of Chromatography*, 1986, "Hydrocarbon Group Analysis of Gasolines with Microbore Supercritical Fluid Chromatography and Flame Ionization Detector".
Jones, Markides, Bradshaw, Lee, *Chromatography Forum*, May-Jun. 1986, "Contemporary Capillary Column Technology for Chromatography".
Hewlett-Packard Technical Note on 5880A Gas Chromatograph on Simulated Distillation.

*Primary Examiner*—Robert A. Wax
*Assistant Examiner*—T. J. Wallen
*Attorney, Agent, or Firm*—Joseph H. Smith

[57] ABSTRACT

A method is provided which can be used to accurately determine the boiling points of middle to heavy petroleum residues (AEBP of 250–1400 degrees F.) using temperatures well below their decomposition temperatures. The method involves the use of a capillary supercritical fluid chromatography apparatus, and consists of a calibration run followed by a measurement run. First, a temperature T1 (between 100 degrees C. and 180 degrees C.) is established in a gas chromatographic (GC) oven of the SFC apparatus, and that temperature is maintained throughout the method. Then a calibration run is performed on a calibration standard using a pressure program, and a calibration function is calculated using the known boiling points of the calibration standard. Then the test sample is run using the same pressure program and the calibration function is used to calculate the boiling point distribution of the test sample.

6 Claims, 8 Drawing Sheets

| TABLE | SIMDIS REPORT FOR HEAVY PETROLEUM FRACTIONS * | | | |
|---|---|---|---|---|
| % Off | DISTACT Fraction | | Atmospheric Residuum | |
| | retention time (min) | temperature (°F) | retention time (min) | temperature (°F) |
| IBP** | 9.37 | 846.9 | 5.63 | 653.0 |
| 5.00 | 15.50 | 1087.1 | 6.28 | 692.3 |
| 10.00 | 16.01 | 1102.6 | 6.76 | 718.6 |
| 15.00 | 16.35 | 1113.9 | 7.31 | 748.2 |
| 20.00 | 16.64 | 1122.2 | 7.75 | 771.1 |
| 25.00 | 16.89 | 1129.7 | 8.18 | 791.3 |
| 30.00 | 17.13 | 1136.7 | 8.71 | 816.5 |
| 35.00 | 17.35 | 1143.0 | 9.18 | 837.9 |
| 40.00 | 17.56 | 1148.8 | 9.77 | 864.4 |
| 45.00 | 17.77 | 1154.5 | 10.43 | 893.3 |
| 50.00 | 17.98 | 1160.4 | 11.29 | 930.3 |
| 55.00 | 18.19 | 1166.1 | 12.36 | 974.3 |
| 60.00 | 18.41 | 1171.8 | 13.57 | 1020.3 |
| 65.00 | 18.63 | 1177.7 | 14.79 | 1064.5 |
| 70.00 | 18.87 | 1184.0 | 16.04 | 1103.7 |
| 75.00 | 19.12 | 1190.5 | 17.36 | 1143.4 |
| 80.00 | 19.40 | 1197.5 | 18.78 | 1181.7 |
| 85.00 | 19.72 | 1204.2 | 20.33 | 1217.8 |
| 90.00 | 20.13 | 1212.9 | 22.29 | 1262.4 |
| 95.00 | 20.75 | 1227.8 | 24.88 | 1320.8 |
| FBP Ψ | 22.59 | 1269.3 | 29.09 | 1415.5 |

\* chromatographic conditions same as Figure 1; for samples, see Experimental section

\*\* IBP = initial boiling point      Ψ FBP = final boiling point

Fig. 4

| TABLE RETENTION TIMES OF STANDARDS OVER A 17-DAY PERIOD * | | | |
|---|---|---|---|
| | Retention Time (min) | | |
| n-Alkane | 11 April | 23 April | 28 April |
| C10 | 3.26 | 3.27 | 3.25 |
| C12 | 3.50 | 3.51 | 3.50 |
| C14 | 3.86 | 3.86 | 3.86 |
| C16 | 4.33 | 4.34 | 4.34 |
| C18 | 4.92 | 4.93 | 4.93 |
| C20 | 5.60 | 5.61 | 5.61 |
| C22 | 6.33 | 6.33 | 6.33 |
| C24 | 7.07 | 7.08 | 7.07 |
| C26 | 7.81 | 7.81 | 7.80 |
| C28 | 8.53 | 8.53 | 8.51 |
| C30 | 9.22 | 9.22 | 9.19 |
| C32 | 9.89 | 9.89 | 9.85 |
| C34 | 10.54 | 10.53 | 10.49 |
| C36 | 11.15 | 11.16 | 11.10 |
| C38 | 11.75 | 11.77 | 11.70 |
| * conditions same as Figure 1; column was kept at 100 °C when not in use | | | |

Fig. 6C  RETENTION TIME (MIN)

Fig. 7a  TIME (MIN)

Fig. 7b

TABLE: COMPARISON OF ATMOSPHERIC EQUIVALENT BOILING POINTS OBTAINED BY GC AND SFC FOR THREE LUBRICATING OILS

ATMOSPHERIC EQUIVALENT BOILING POINT, °F

| WT % DISTILLED | SAMPLE A GC | SAMPLE A SFC* | SAMPLE B GC | SAMPLE B SFC* | SAMPLE C GC | SAMPLE C SFC** |
|---|---|---|---|---|---|---|
| IBP | 744 | 629 | 674 | 677 | 212 | 538 |
| 5 | 797 | 811 | 775 | 764 | 638 | 657 |
| 25 | 873 | 869 | 836 | 824 | 796 | 793 |
| 50 | 920 | 929 | 877 | 862 | 854 | 846 |
| 75 | 962 | 968 | 921 | 905 | 904 | 900 |
| 95 | 1024 | 1029 | 998 | 975 | 985 | 1012 |
| FBP | 1079 | 1087 | 1054 | 1028 | 1050 | 1183 |

Conditions: see Experimental and text.
* Pressure program: 200 to 5500 psi in 20 min.
** Pressure program: 850 to 5500 psi in 26 min.

SIMULATED DISTILLATION OF PETROLEUM RESIDUES BY CAPILLARY SFC

BACKGROUND OF THE INVENTION

This invention pertains to capillary supercritical fluid chromatography (SFC), and particularly to capillary SFC for simulated distillation of petroleum residues having boiling points higher than 250 degrees C.

Distillation is the most widely used separation technique in the petroleum industry. Knowledge of boiling point distribution data for crude oils and refined petroleum products is essential for process control and quality assurance. Distillation procedures, standardized by the American Society for Testing and Materials (ASTM), date back to 1926. The classical distillation procedures such as the ASTM D86, the D1160, and the D2892 require large sample sizes and are generally less precise than simulated distillation (SIMDIS) methods based on gas chromatography (GC) (See ASTM standards D87, "Annual Book of ASTM Standards", Vol. 5.01, pp. 8-27, pp. 603-615; Vol. 5.02 pp. 813-850, pp. 791-799; Vol. 5.03, pp. 442-455.

In GC-SIMDIS, the gas chromatograph can be regarded as a highly efficient microdistillation unit, while chromatography under low resolution conditions is performed. The applicability of GC-SIMDIS to the analysis of petroleum derived materials and coal-derived liquids is now well established and it has been demonstrated that GC-SIMDIS data are in excellent agreement with actual distillation methods. GC-SIMDIS methods, adopted by the ASTM since 1973, involve the use of packed columns with a nonpolar silicone gum as a stationary phase. However, the upper limit of the boiling range covered by these methods is approximately 1000 degrees Fahrenheit atmospheric equivalent boiling point (AEBP) (Hereinafter, the Fahrenheit scale is used for boiling point distribution data in accordance with ASTM methods and most other publications. Experimental conditions, as is the custom, are cited in degrees Celsius. In addition, when the term "boiling point" is used, it will mean the AEBP.).

Efforts have been undertaken to extend the scope of the GC-SIMDIS methods by employing short, thin-film capillary columns. The reason is that these columns are more favorable for the analysis of high boiling fractions because of their increased phase ratio which allows for a reduction of analysis time and column elution temperature. For instance, Trestianu et al (See HRC & CC, 1985, 8,771) found that elution temperatures on capillary columns were 100 degrees C. lower than on corresponding packed columns. Also, it has been demonstrated that capillary GC, combined with cold, on-column injection, is suitable for SIMDIS of petroleum fractions ranging from 300 to 1470 degrees F. AEBP. In this approach, however, column temperatures of up to 430 degrees C. are employed. Also by using a new type of aluminum-clad, fused silica columns for capillary GC, crude oils were chromatographed with temperatures up to 440 degrees C. These high column temperatures, however, far exceed the temperature limit <> 350 degrees C.) at which sample decomposition may occur and are of great concern to petroleum chemists.

The search for milder operating conditions, i.e. lower temperatures, has led to the development of SIMDIS methods other than GC, e.g. gel permeation chromatography (GPC), vacuum thermal gravimetric analysis (VTGA). In GPC, difficulties arise in the correlation of the "molecular size" distribution data to AEBP. VTGA techniques were described in the literature by Southern et al. (Anal. Chem., 1985, 57,303) and by Mondragon and Ouchi (Fuel, 1984, 63,61). The first group employed the Maxwell-Bonell equation for calculation of AEBP, while the latter used a calibration method based on actual distillation data from the ASTM D1160 method. The VTGA method performed by the latter group utilized a different approach, i.e. VTGA temperatures were calibrated with n-alkane standards in a similar fashion as boiling points of standards are related to retention times in GC-SIMDIS methods. Modification of the conventional TGA instrument for vacuum operation reduced the sample exposure to high temperatures and allowed for AEBP determinations up to approximately 1400 degrees F.

However, it is clear that none of the above approaches is completely satisfactory for high boiling point petroleum fractions due to high column temperatures.

SUMMARY OF THE INVENTION

In accordance with preferred embodiments of the invention, a method is provided which can be used to accurately determine the boiling points of middle to heavy petroleum residues (AEBP 250-1400 degrees F.) using temperatures well below their decomposition temperatures. In the preferred mode, the method involves the use of a capillary supercritical fluid chromatography apparatus, and is performed according to the following steps. First, a temperature T1 is established in a gas chromatographic (GC) oven of the SFC apparatus, and that temperature is maintained throughout the run. The temperature T1 is in the range of 100 degrees C. to 180 degrees C., well below the typical column temperatures of 350 to 430 degrees C. typically used for simulated distillation of heavy residues by gas chromatography. Next, at the injection side of a chromatographic column located in the GC oven, a pressure program is established which is a function of time, p(t). The pressure program begins at an initial pressure p1 and ends at a final pressure p2, with the program taking place over a duration of time t1 beginning when a sample is injected into the column. Then a first (calibration) sample is injected into the column, the sample being composed of materials having known boiling points. The calibration sample is then eluted from the exit end of the column over the period of time t1. The eluted sample is then detected using a flame ionization detector during the time t1 to obtain a chromatogram of the first sample. The retention times of peaks detected in the chromatogram of the calibration sample are then correlated with the corresponding known boiling points for the materials comprising the first sample, to obtain a calibration function relating retention time to boiling point. The pressure program p(t) is then reinitialized after the time t1, with the pressure program beginning when a second (test) sample is injected into the column. The second (test) sample is then injected into the column, and this test sample is eluted from the column over a second period of time equal to t1. The sample eluted during the second period of time is then detected using an FID to obtain a chromatogram of the test sample. Finally, a boiling point distribution is calculated for the test sample using the calibration function. In the preferred mode, an integral restrictor is used at the exit end of the capillary column.

Applications of the above method to medium to heavy petroleum residues has been extremely successful in yeilding definitive boiling point information. Also, comparison of boiling points derived by the above method with boiling points derived from capillary GC shows a very good correlation, thus validating the SFC approach.

BRIEF DESCRIPTION OF THE DRAWINGS

Shown in FIG. 1 is a capillary SFC apparatus.

Shown in FIG. 2 is a chromatogram of a calibration sample using capillary SFC.

Shown in FIG. 3a is a graph illustrating a reconstructed area slice chromatogram and a boiling point distribution plotted as a function of temperature using capillary SFC according to the method of the invention on a first (exemplary) test sample.

Shown in FIG. 3b is a graph illustrating a reconstructed area slice chromatogram and a boiling point distribution plotted as a function of temperature using capillary SFC according to the method of the invention on a second (exemplary) test sample.

Shown in FIG. 4 is a table illustrating the results of simulated distillation according to the method of the invention for the samples of FIGS. 3a and 3b.

Shown in FIG. 5 is a table illustrating retention times of a set of n-alkane standards over a period of time.

Shown in FIGS. 6a–6c are chromatograms of a calibration sample (PE-740), illustrating the effects of oven temperature on resolution.

Shown in FIGS. 7a and 7b are chromatograms illustrating the effects of starting pressure for a pressure program.

Shown in FIG. 8 is a table comparing atmospheric equivalent boiling points obtained by GC and SFC for three lubricating oils.

Shown in FIG. 9 is a graph correlating retention times to boiling points for a series of standards.

DETAILED DESCRIPTION OF THE PREFERRED EMBODIMENTS

Figure 1:
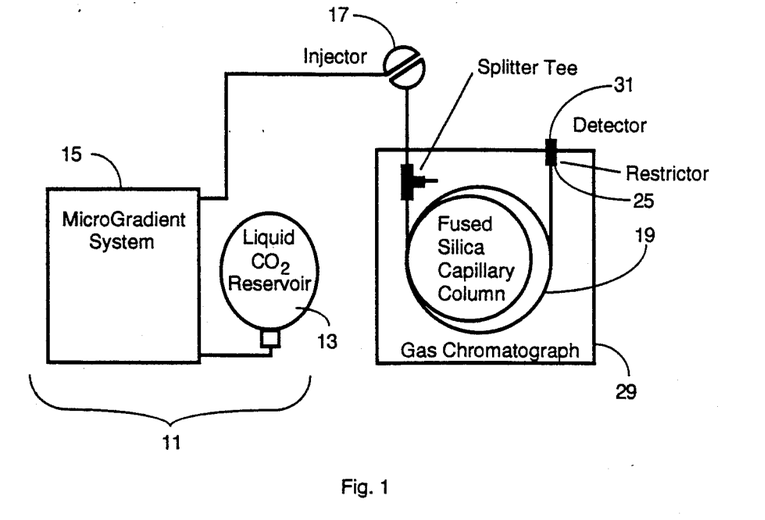

Shown in FIG. 1 is a system for performing capillary SFC. The system includes a fluid delivery system 11 made up of a liquid carbon dioxide reservoir 13 and a high pressure pump 15 having the capability of pressure programming. In the preferred mode, the pump 15 is a Brownlee Labs Model MG with revision J software for permitting the pressure programming, which allows for filling of the pump without cooling. Other pumping systems may also be used provided they have adequate and precise pressure control. The carbon dioxide used is typically of a high quality suitable for SFC and is supplied from a 50-lb cylinder having an eductor tube (e.g. such as is available from Scott Specialty Gases, Plumsteadville, Pa).

The outlet of the pump 15 is connected to a high pressure, HPLC-type injector 17, typically via stainless steel capillary tubing and a low dead volume in-line filter (not shown). The injector 17 is for introducing very small volumes of sample into a capillary column 19. Typically, however, injectors have volumes as large as 0.1 to 0.5 microliters, and smaller volumes are generally desired for capillary SFC. Hence, a splitter 21 is used at the input to the column. In the preferred mode, the outlet side of the splitter is connected to a one meter by 25 micrometer i.d. piece of fused silica tubing to yield a desired split ratio of 1:10, although other split ratios might well be used. The split ratio can vary depending on the desired sample volume to be delivered to the column, and is determined by the ratio of the restrictor diameter at the end of the column to the splitter diameter. (The restrictor at the end of the column will be described subsequently) Also in the preferred mode, the injector 17 is mounted on top of a gas chromatograph 29 (GC) having a flame ionization detector (FID) 31 associated therewith. The preferred GC is a Model 5890 gas chromatograph such as is available from Hewlett-Packard Company. Also in the preferred mode, the FID is maintained at about 350 degrees C., and the splitter is maintained at that same temperature by means of a manifold attached to the FID. The preferred column 19 is a 10 meter by 50 micrometer i.d. capillary with a 0.2 micrometer film thickness, the film typically being comprised of 5% diphenyl, 95% dimethyl-polysiloxane (available as DB-5 from J & W Scientific of Folsom, CA).

At the end of the column 19, a flow restrictor 25 is provided which is used to maintain the mobile phase at or above the critical pressure throughout the column and which also provides the necessary sample introduction interface between the column and the FID. In the preferred mode, the restrictor is an integral restrictor as is known in the art, for example, see "Integral Pressure Restrictor for Capillary SFC", by E. J. Guthrie and H. E. Schwartz, in J. Chromatographic Science, Vol. 14, June 1986. Such an integral restrictor can be fabricated according to the following process: The detector end of the SFC capillary column is heated and allowed to gently close using either a butane/nitrous oxide miniature gas torch or an oxy-acetylene welding torch. A small, high-temperature flame is preferable. The tubing is heated such that the fused silica slowly draws closed in a viscous flow, producing a well-defined, conical closure. The capillary column is subsequently pressurized with liquid carbon dioxide to a desired pressure (i.e. 1800 psi) using the supercritical fluid pump. The closed end of the capillary tube is then gently abraded by hand used a wet, 3200-grit, abrasive sheet, slowly removing the excess fused silica from the terminal end of the column until a conical closure is reached. Gas bubbles excaping from the column indicated when this point has been reached. Although in the preferred mode such an integral restrictor is used, another preferred mode is to use a separate restrictor which is attached to the column that is manufactured in a similar manner and attached appropriately to avoid dead volumes. Henceforth, for the purpose of discussion, both of these kinds of restrictors which are constructed according to the specifications described in the Guthrie and Schwartz reference above will be described as "integral restrictors", since they are interchangeable for all practical purposes. Other restrictors known in the art of capillary SFC may also work. In operation, the gaseous (carbon dioxide) flow rate through the column (and restrictor) is generally about 3.4 ml/min at 1800 psi and room temperature. In the pressure range of 2000 to 5000 psi at 100 degrees C., the average linear velocity of the mobile phase through the capillary column typically varies between 4.2 and 5.2 cm/sec. Also, as a matter of construction, the restrictor is inserted into the FID jet such that the end of the restrictor is even with the jet tip. Also, although the injector is shown in FIG. 1. as being external to the GC oven, in some instances the injector is mounted inside the oven by means of a standoff extension (not shown).

Data acquisition techniques for the above system are well known in the art and can be accomplished, for example, using an IBM compatible computer via an A/D interface such as the model 7625 available from Nelson Analytical. Similarly, Nelson Analytical model 2880 simulated distillation software and model 2600 chromatography software can be used for data processing.

METHOD OF THE INVENTION

According to the method, at least two complete cycles are performed, a first cycle which uses capillary SFC on a calibration standard having known boiling points, in order to correlate the SFC retention times with the boiling points; and a second cycle which is a simulated distillation on the sample under test followed by a calculation routine to determine the boiling point distribution of the sample under test. The detailed steps of the method are as follows:

1. establishing a GC oven temperature of T1 and maintaining it at that temperature;
2. establishing a pressure program p(t) in the system as a function of time beginning at an initial pressure p1 and ending at a final pressure p2, the pressure program to take place over a duration of time t1, the time of the run, with the time beginning at sample injection;
3. injecting a first (calibration) sample into the column which is composed of materials having known boiling points;
4. eluting the calibration sample from the column/restrictor over the period t1;
5. detecting the sample eluted from the column/restrictor during the time t1 to obtain a chromatogram;
6. comparing peaks in the chromatogram with known boiling points for the materials comprising the calibration sample, to obtain a calibration function relating retention time to boiling points;
7. reinitiating the pressure program as in step 3;
8. injecting a second (test) sample into the column;
9. eluting the test sample from the column/restrictor over a period of time equal to t1;
10. detecting the test sample eluted during the period t1 to obtain a second chromatogram; and
11. calculating a boiling point distribution for the test sample using the calibration function of step 6.

Steps 7 through 11 can then be repeated as desired for different samples, until recalibration is required.

As is known in the art, the integrated detector response is proportional to the percentage of sample distilled off, thereby providing a distribution of "percentage off" as a function of time. The calibration function can then be used to convert this distribution of retention times to a distribution of boiling points.

In the preferred mode, it is desired that the oven temperature T1 be low enough to avoid thermal decomposition of the samples being tested. On the other hand, the column temperature should be high enough to provide the desired resolution and to avoid soluability problems often associated with heavy residues at low temperatures. Generally, there is an optimal range of temperatures for performing simulated distillation using capillary SFC. For middle to heavy petroleum residues (having boiling points over about 250 degrees F. up to about 1450 degrees F.), the optimal range of oven temperatures appears to be 100–180 degrees C., lower temperatures being preferred in order to avoid thermal decomposition.

The range of starting pressures p1 generally varies from a low of about 850 psi to about 2000 psi, with the preferred being 2000 psi for fractions having boiling points over 1000 degrees F. Lower starting pressures, e.g. 850 psi, are generally used for lower boiling point materials, otherwise these residues are eluted immediately at the beginning of a run and the accuracy of the boiling point determination is impaired. Generally the upper limit p2 for the programmed pressure maximum is determined by the constraints of apparatus, and at the present time results in a practical maximum of about 5500 psi. It is expected that future systems may be able to increase the maximum pressure to about 7000 psi, or higher, in order to elute even higher boiling point materials within a reasonable time. The pressure program function p(t) in the preferred mode is a linear ramp from p1 to p2, followed by a period of time at the final system pressure p2 (i.e. p(t) is isobaric). In the preferred embodiment, elution time t1 was chosen arbitrarily at 30 minutes as a reasonable time for a run, with the ramp from p1 to p2 taking place over a 20 minute period, with the final system pressure p2 being maintained for a period of 10 minutes.

EXPERIMENTAL RESULTS/EXAMPLES

Figure 2:
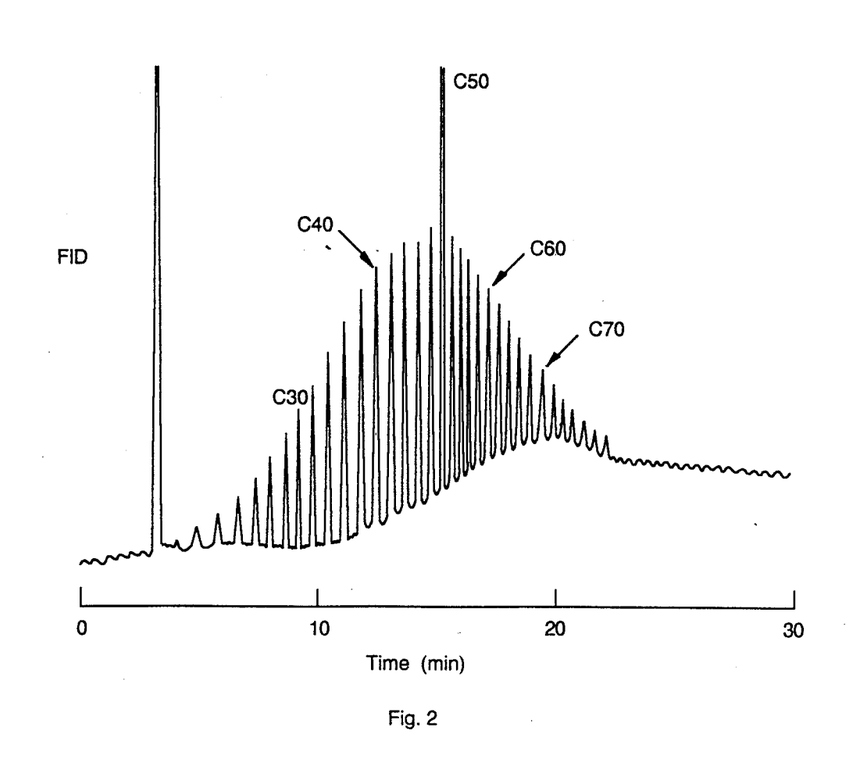

In FIG. 2, a linear pressure program for a low molecular weight polyethylene calibration standard (PE-740, available for Pressure Chemical Company), was performed according to the method over the range from 2000 to 5500 psi, over a 20 minute period; then the pressure was held at 5500 psi for 10 minutes. Thirty-five peaks can be discerned, the retention times of which subsequently can be correlated with boiling points using boiling point data obtained from a publication of the American Petroleum Institute (API) "Thermodynamic Tables, Hydrocarbons, Vol. V" API Research Project No. 44, Tables 23-2-(1.101)-k, Thermodynamic Research Center, Texas A&M Univ., 1974 pp. k-10.10-k-10.60). standard tables available from the American Petroleum Institute (API). In this calibration sample, pentacontane (C50) was used as a marker for the identification of the alkene peaks in the PE-740 sample. The even-numbered alkene oligomers of PE-740 are, under the chosen conditions, nearly equally spaced throughout the chromatogram. The C80 peak elutes at about 21 minutes and is one of the last peaks visible in the chromatogram.

It can also be seen in FIG. 2 that there is a slight baseline offset in the chromatogram. The importance of baseline correction when real samples are analyzed by GC-SIMDIS is well documented in the art. Hence, the software used in the present invention permits correction for background effects by means of a baseline subtraction routine.

In the present invention, separations were performed at an optimal oven temperature of 100 degrees C., a far lower temperature than can be used for SIMDIS by gas chromatography.

The SFC method was applied to two samples that could not be successfully analyzed with conventional SIMDIS methods based on gas chromatography. The samples originated from a domestic (Altamont, Utah) crude oil. The "atmospheric residuum" was obtained by removing low-boiling fractions (less than 650 degrees F.) from the crude by conventional column distillation at atmospheric pressure. The atmospheric residuum, in turn, was then used as a feedstock for short-path vacuum distillation resulting in a well-defined residue and distillate cut for each temperature, known as a DISTACT fraction in the art.

Figure 3A:
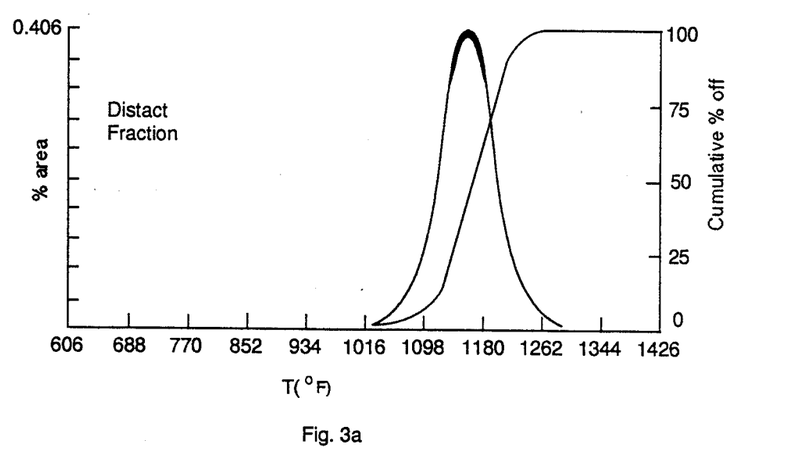
Figure 3B:
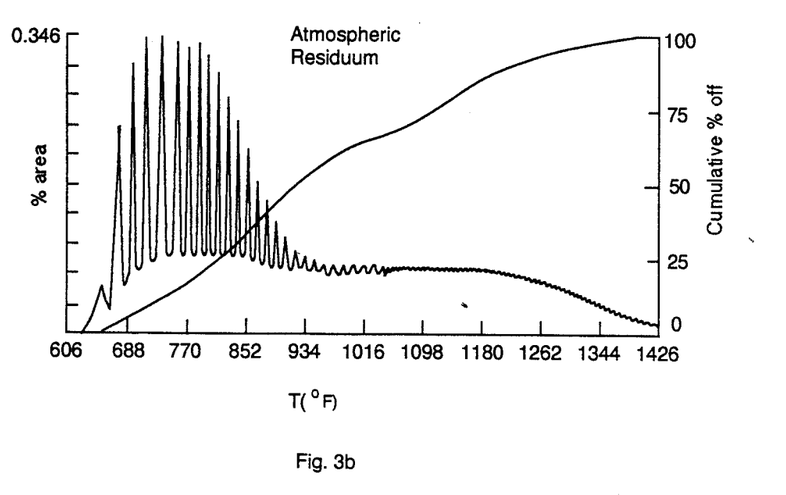

The computer-generated, reconstructed area-slice chromatograms and boiling-point distributions are shown for the above petroleum samples in FIGS. 3a and 3b. The chromatograms are normalized such that the largest percent-area value is shown at the top of the scale. The atmospheric-residuum sample has many peaks eluting in the early part of the chromatogram, indicating that the original crude oil has a high alkane content, which is well known for crude oil for Altamont. On the other hand, in the case of the high boiling DISTACT fraction (FIG. 3a), fine structure cannot be observed.

It should be noted the DISTACT fraction under the present conditions was fully recovered from the column. This result was obtained by using hexadecane, which did not coelute with the petroleum fraction, as an internal standard. For the atmospheric residuum, only 3% did not elute from the column.

Figure 4:
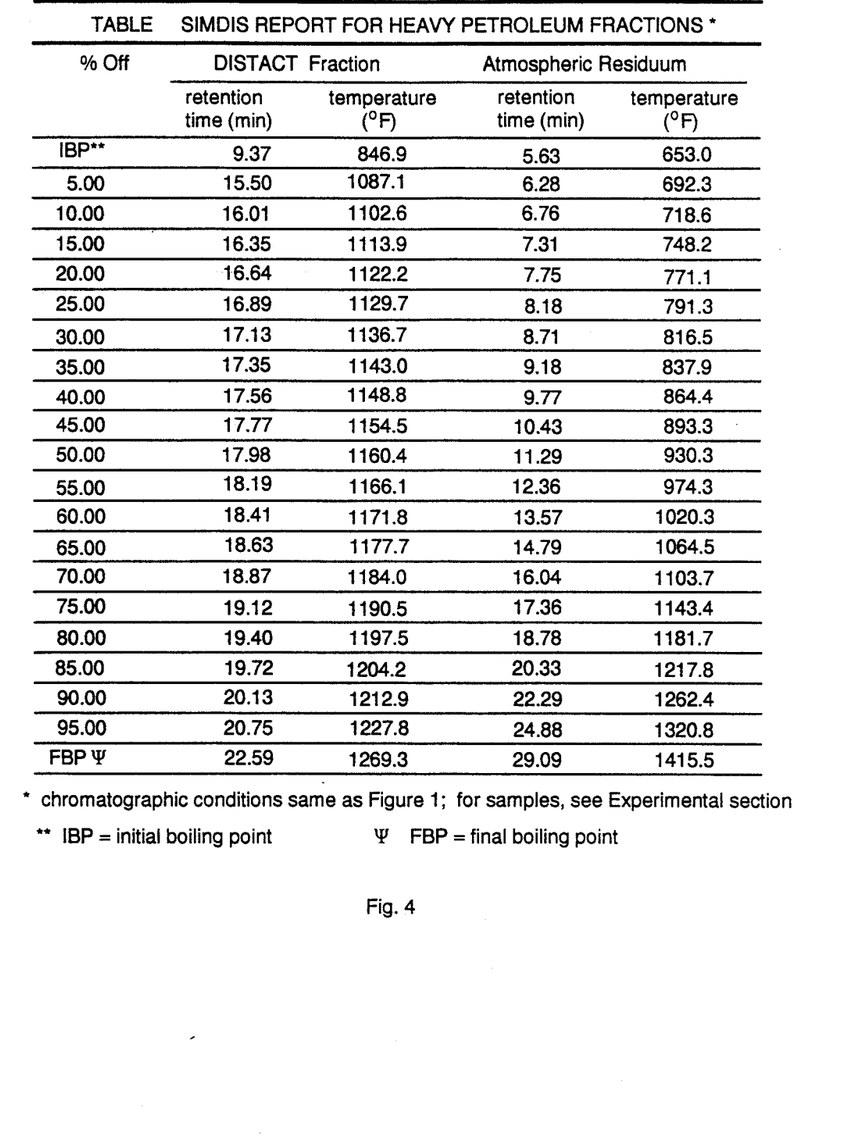

More-detailed information is shown in the Table of FIG. 4, in which the SFC-SIMDIS results are displayed as a "% Off" tabulation (i.e. the percentage distilled off). Also shown are the corresponding retention times observed during the SFC run. Distillation percentages are given in 5% increments. The initial and final boiling points cannot be determined with good accuracy. For diagnostic purposes, therefore, the 5% to 95% interval is taken. For the atmospheric residuum, 95% of the sample would distill at 1320 degrees F. Further, it appears that the final boiling point is over 1400 degrees F.

Figure 5:
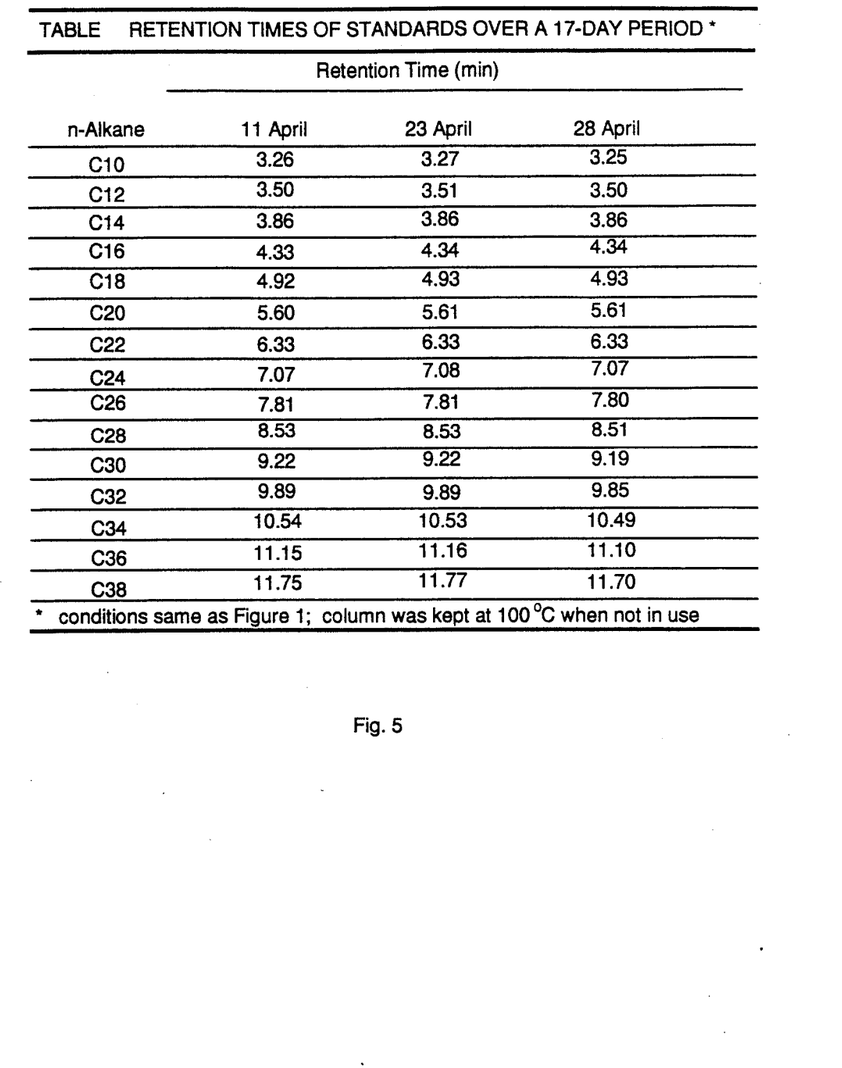

Because the boiling-point distribution is based on the retention times of standard components (in this case PE-740), good chromatographic precision of retention data is a prerequisite for SIMDIS analysis. With the above method and apparatus, excellent run-to-run reproducibility is obtained with the capillary-SFC/integral restrictor system. Under conditions similar to those in FIG. 2, the percent relative standard deviation of retention times for 10 consecutive runs ranged from 0.12% to 0.28%. In SIMDIS analysis, day-to-day reproducibility is important in deciding the frequency at which calibration must be performed. The table of FIG. 5 shows retention time data for a series of alkanes eluting in a relatively early part of the chromatogram. Chromatographically, it is known that precision improves with increasing retention during a temperature (GC) or solvent (HPLC) program. Likewise, in SFC, precision improves during a pressure gradient. Therefore, the early part of the chromatogram is the most informative with regard to long-term precision. FIG. 5 shows that during a period of three weeks, retention times remain virtually unchanged. Consequently, it appears that calibration in SIMDIS analysis by means of capillary SFC using an integral restrictor does not have to be performed on a day-to-day basis.

Figure 6A:
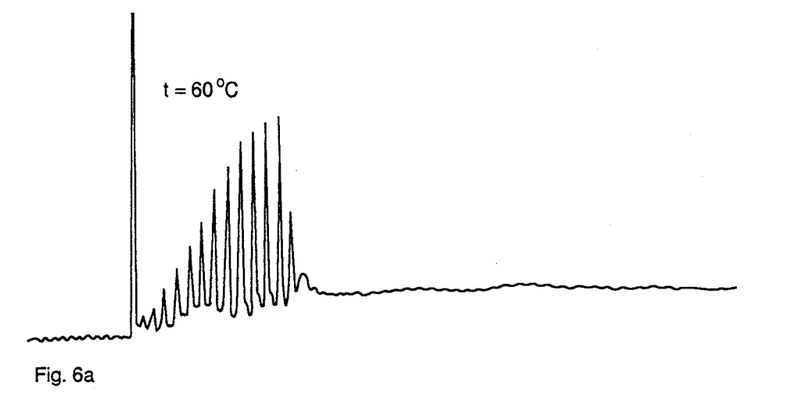
Figure 6B:
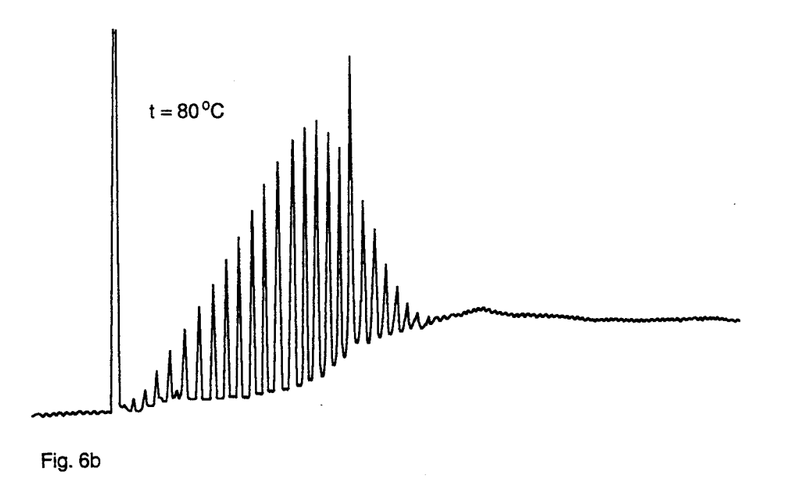
Figure 6C:
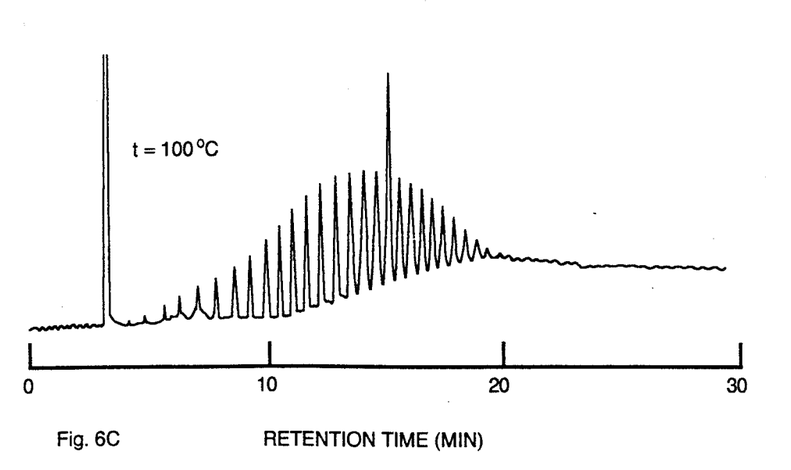

From the results of another set of experiments illustrated in FIGS. 6a through 6c, the influence of temperature on retention and resolution is seen. In these figures chromatograms of the calibration standard (PE-740) are shown at three different temperatures (with a different scale than was used in FIG. 1). In all cases the same pressure program was run, i.e. from 2000 to 5500 psi, while the injection valve was mounted inside the GC oven to prevent undesirable temperature gradients. Since both the inlet (injector) and outlet restrictor were kept at the same temperature (350 degrees F.), it can be assumed that the split ratio remained constant during the experiments. A marker, again pentacontane (C-50), was added to the sample as before described to identify the peaks. It can be seen that at 60 degrees C., poor resolution is obtained for the higher carbon number alkanes. The C-50 marker cannot be discerned from the other peaks. A remarkable improvement in resolution appears at higher temperature, as can be seen in FIGS. 6B and 6C. At higher temperatures than 100 degrees C. (not shown), no significant improvement in resolution was obtained for this particular standard. Higher temperatures, however, have proven to lead to more favorable recoveries of sample from the column for higher boiling point materials. For example, in one experiment under isobaric conditions (5000 psi), higher recoveries of pentacontane have been demonstrated for capillary SFC at temperatures up to 180 degrees C. using the SFC apparatus as described above. (Pentacontane has a boiling point of 1067 degrees F.)

Figure 7A:
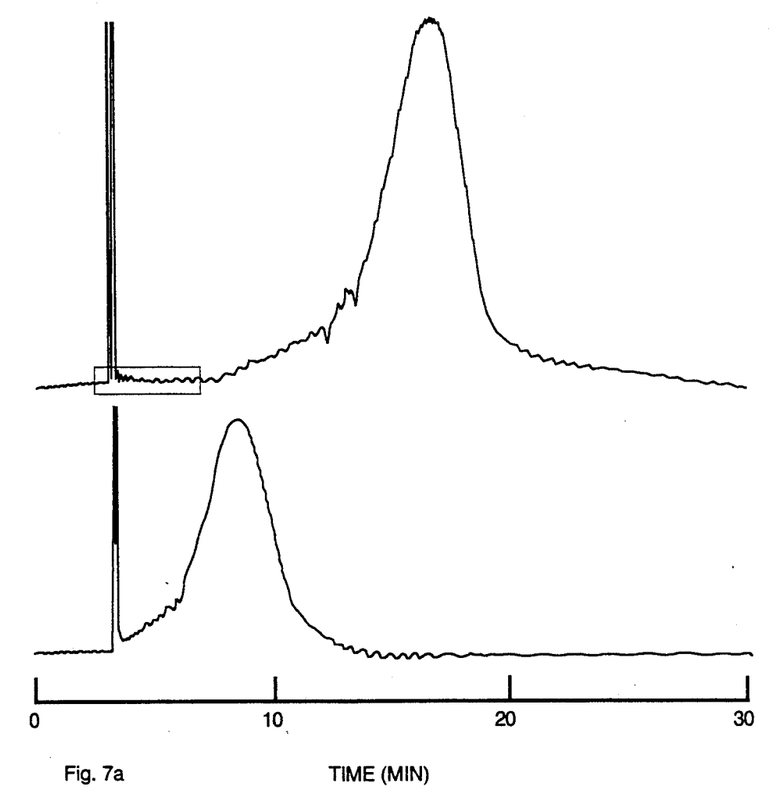
Figure 7B:
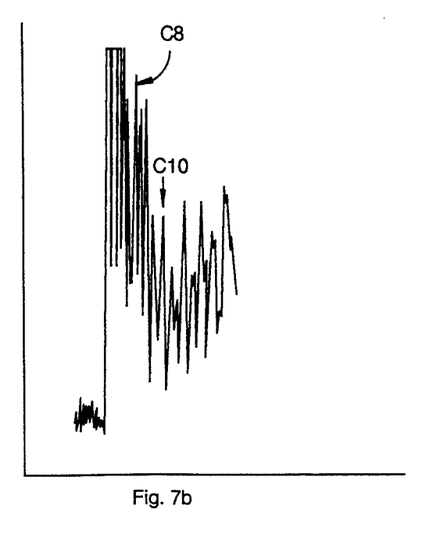

In terms of the scope of the SFC SIMDIS method, the lower limit of boiling points which can be discerned is determined by the resolution of the solvent peak and the first eluting sample peak. In the present SFC method, the lower limit is dependent on the initial column pressure. The role of pressure on the separation of early eluting sample components is illustrated in FIGS. 7a and 7b. In general, it is favorable to initiate the pressure program at the lowest possible pressure. When using carbon dioxide, this corresponds to about 800 psi, i.e. the vapor pressure of carbon dioxide in the supply cylinder at room temperature. However, in many cases (e.g. high-boiling DISTACT cuts) this would make the analysis unnecessarily long, since no sample components elute in the early part of the chromatogram.

In FIG. 7a, the chromatogram of a lube oil base stock containing a kerosene contaminant is shown with two pressure programs. Initiating the pressure program at 2000 psi (lower trace in FIG. 7a), causes an overlap of the early eluting peaks, which would result in inaccurate boiling point distribution data. By starting the pressure program at 850 psi (upper trace in FIG. 7a), while maintaining the same pressure ramp, i.e. 165 psi/min, the separation in the early part of the chromatogram is much improved. The insert (FIG. 7b) shows that under these conditions, n-octane (boiling point 257 degrees F.) is resolved from a solvent peak. Hence, the SFC method is applicable to samples with initial boiling points of approximately 250 degrees F. Those skilled in the art will recognize, however, that such temperatures are well within the purview of other methods, and that the greater utility of capillary SFC for simulated distillation is for higher boiling point residues, such as those having boiling points in the range of 650 degrees C. to about 1400 degrees C.

Comparison of SFC - SIMDIS with GC - SIMDIS

Although the SFC approach can be validated using direct comparison with known standards for classical distillation procedures, such procedures are generally less precise than SIMDIS based on GC. Hence, as a validation of the present method, the results of the SFC-SIMDIS approach have been compared with the results of GC-SIMDIS.

Figure 8:
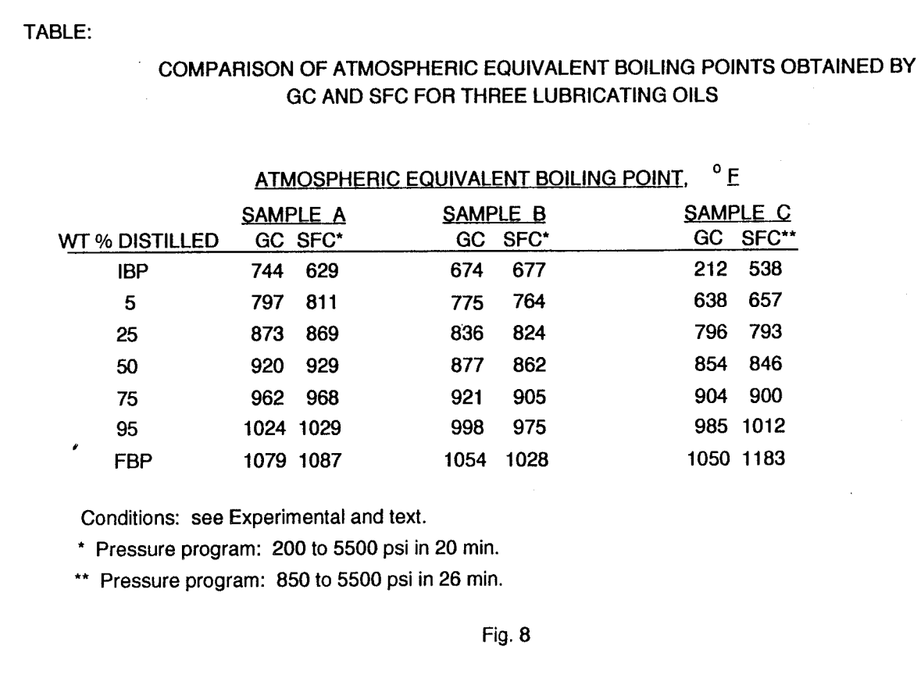

As pointed out earlier, standard GC-SIMDIS methods are confined to AEBP information up to approximately 1000 degrees F. Therefore, lube oil base stocks, covering a boiling point range from approximately 500–1000 degrees F., serve as good examples for the GC and SFC method comparison. In the Table of FIG.

8, the results obtained by GC are compared to those with capillary SFC for three lubricating oils. Data show the initial boiling point (IBP), the AEBP at 5, 25, 50, 75, and 95% distilled, and the final boiling point (FBP). (Sample C contained a small amount of a low boiling contaminant.)

It can be seen from the Table of FIG. 8 that, except for the IBP and FBP, the GC and SFC derived data correspond well. It should be noted that the results were subject to interlaboratory variations. For example, the SFC data were acquired and processed with the Nelson Analytical system, while the GC data were obtained with a Hewlett-Packard data system. The difficulties in accurately determining the IBP and FBP are well documented in the art and are closely related to the software algorithms used to define the peak areas slices and the method employed for baseline subtraction. As was pointed out before, the SFC method is limited to samples with the initial boiling point higher than 250 degrees F. Sample C (IBP=212 degrees F. as determined by GC), therefore, may be beyond the range of the present method.

Next, a regression analysis was carried out to correlate the SFC and GC data of FIG. 8. A least squares fit of the data points in the 5–95% distilled range gave the following equation within the 95% confidence interval:

AEBP by SFC=(0.98±0.07) AEBP by GC+(13±66)

The correlation coefficient was 0.991. These data indicate that the calculated slope and intercept do not differ significantly from the "ideal" values of 1 and 0, respectively. There is, therefore, no evidence for a systematic difference between the two sets of results, so that indeed capillary SFC-SIMDIS is an acceptable approach to determining boiling points.

Figure 9:
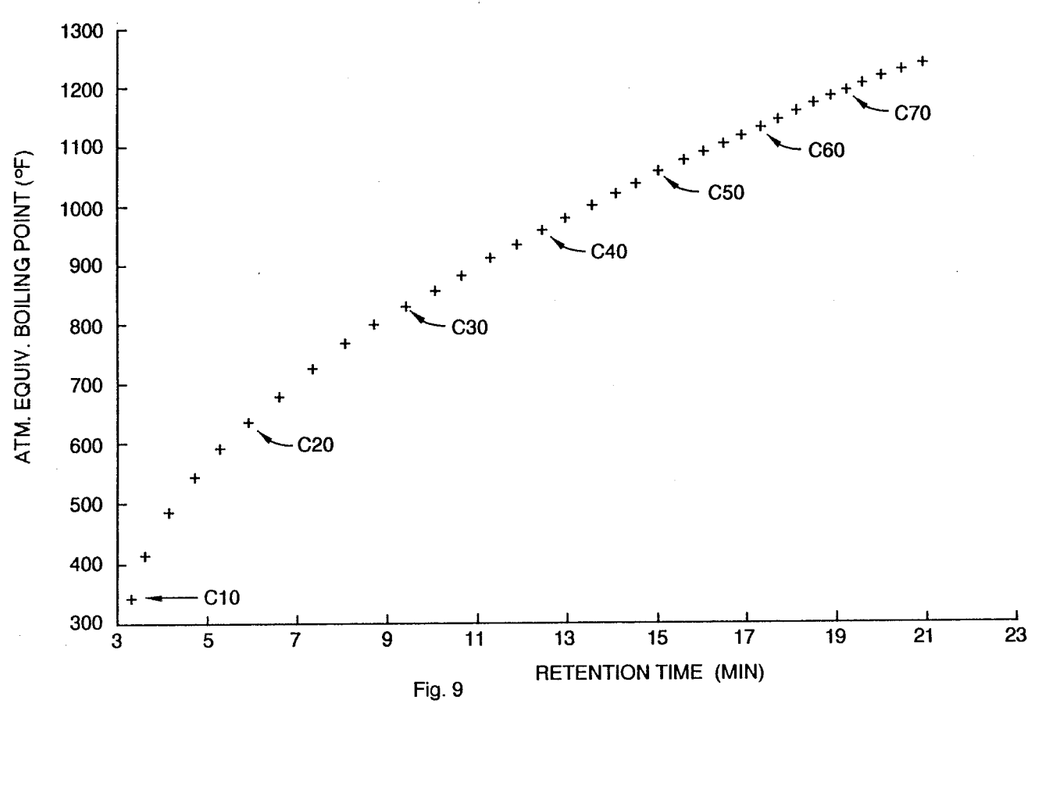

Those skilled in the art will also appreciate that the method is not limited to a particular calibration standard. For example, other appropriate standards include low molecular weight polyethylene standards and mixtures of alkane standards. For example, the calibration curve of FIG. 9 was obtained by performing two calibration runs using the calibration portion of the method of the invention, one run using PE-740 and the other using a mixture of low boiling alkane standards (C10–C20). Boiling point data for performing the calibration run were obtained from a publication of the API as described earlier. It can be seen that under conditions of linear pressure programming, a strong curvature in the lower boiling point range is obtained, while the curve becomes almost linear in the higher boiling point range. The data point with the highest boiling point (1233 degrees F.) in FIG. 9 corresponds to an alkane with a carbon number of 78. The Nelson Analytical software allows for either a point-by-point or a quadratic or cubic curve fit through the calibration data points. The actual boiling point distribution interval (e.g. 606–1426 degree F. illustrated in FIG. 3) was determined by the chromatographic run time. The boiling point information exceeding 1233 degrees F. was obtained by extrapolation of the curve-fitted calibration data. This particular calibration was the one used for the validation study comparing GC-SIMDIS with SFC-SIMDIS above.

Those skilled in the art will appreciate that the operating parameters given above in the examples are meant to be illustrative, rather than limiting. For example, although the FID was operated at 350 degrees C., the FID will operate over a range of temperatures, typically from 300 degrees C. to 400 degrees C. Similarly, capillary columns having a different stationary phase may be used, for example DB-1 available from J & W Scientific, which is 100% dimethyl-polysiloxane. Also, the length and diameter of the column may be varied, depending on the desired resolution and operating time. (Resolution is typically specified by the ASTM, see e.g. ASTM D 2887, in which resolution is specified be between 3 and 8.) As a practical matter, however, the diameter cannot be varied indefinitely, and as a minimum should be about 50 micrometers. Similarly, the maximum should be about 200 micrometers, with a preferred diameter being in the range of 50 to 100 micrometers. Similarly, the split ratio used will depend on the volume of the injector and diameter of the capillary column. Also, film thickness of the stationary phase may vary considerably depending on the temperatures and materials used. At the present time, typical thicknesses range from about 0.05 micrometers to as much as 1.0 micrometer or more.

What is claimed is:

1. A method for determining boiling points for heavy residues of petroleum by simulated distillation using a supercritical fluid chromatography apparatus, said supercritical fluid chromatography apparatus having a chromatographic column with an injection end and an exit end with a mobile phase located therebetween having a supercritical temperature, said column having at least a portion thereof located in a gas chromatographic oven, comprising the steps of:

establishing a temperature T1 in said gas chromatographic oven, and maintaining that temperature, the temperature T1 being at or above the supercritical temperature of the mobile phase and in a range of 100 degrees C. to 180 degrees C.;

establishing at the injection end of the column, a pressure program p(t) as a function of time t beginning at an initial pressure p1 and ending at a final pressure p2, the program to take place over an interval of time t1, the time t to begin when a sample is injected into the column;

injecting a first sample into the column, said first sample being comprised of materials having known boiling points;

eluting the first sample from the exit end of the column during the time interval t1;

detecting the first sample eluted from the column using flame ionization detection techniques, to obtain a chromatogram of the first sample;

correlating retention time of peaks in the chromatogram of the first sample with the known boiling points for the materials comprising the first sample, to obtain a calibration function relating elution time to boiling point;

reinitiating the pressure program p(t) after the time interval t1, the pressure program to begin when a second sample is injected into the column;

injecting the second sample into the column, said second sample having boiling point over 250 degrees C.;

eluting the second sample from the column over a second interval of time equal to t1;

detecting the second sample eluted during the second interval of time to obtain a chromatogram of the second sample having a set of retention times; and evaluating said calibration function at said retention times of said second sample to obtain a boiling point distribution for the second sample.

2. The method of claim 1 wherein p(t) comprises a linear ramp from p1 to p2.

3. The method of claim 2 wherein p(t) comprises an isobaric region at p2 following the ramp between p1 and p2.

4. The method of claim 1 wherein p1 is in the range of 850 psi to 2000 psi.

5. The method of claim 1 wherein said chromatographic column is a coated capillary column having an integral restrictor at its exit end.

6. A method for determining boiling points for heavy residues of petroleum by simulated distillation using a supercritical fluid chromatography apparatus, said supercritical fluid apparatus having a chromatographic column with an injection end and an exit end with a mobile phase located therebetween having a supercritical point, said column having at least a portion thereof located in a gas chromatographic oven, comprising the steps of:

establishing a temperature T1 in said gas chromatographic oven, and maintaining that temperature;

establishing at the injection end of the column, a pressure program p(t) as a function of time t beginning at an initial pressure p1 and ending at a final pressure p2, the program to take place over an interval of time t1, the time t to begin when a sample is injected into the column;

said temperature T1 and said pressure p(t) such that said mobile phase is in a supercritical thermodynamic phase during at least a portion of said time interval t1;

injecting a first sample into the column, said first sample being comprised of materials containing heavy petroleum residues with known boiling points;

eluting the first sample from the exit end of the column during the time interval t1;

detecting the first sample eluted from the column using flame ionization detection techniques, to obtain a chromatogram of the first sample;

correlating retention time of peaks in the chromatogram of the first sample with the known boiling points for the heavy petroleum residues comprising the first sample, to obtain a calibration function relating elution time to boiling point;

reinitiating the pressure program p(t) after the time interval t1, the pressure program to begin when a second sample is injected into the column;

injecting a second sample into the column;

eluting the second sample from the column over a second interval of time equal to t1;

detecting the second sample eluted during the second interval of time to obtain a chromatogram of the second sample; and calculating a boiling point distribution for peaks in the chromatogram of the second sample using the calibration function.

* * * * *